(12) United States Patent
Campisi et al.

(10) Patent No.: US 12,364,784 B2
(45) Date of Patent: Jul. 22, 2025

(54) WOUND DRESSING FOR TREATMENT OF DAMAGED SKIN

(71) Applicant: FIDIA FARMACEUTICI S.P.A., Abano Terme (IT)

(72) Inventors: Monica Campisi, Abano Terme (IT); Giovanni Gennari, Abano Terme (IT)

(73) Assignee: FIDIA FARMACEUTICI S.p.A., Abano Terme (IT)

( * ) Notice: Subject to any disclaimer, the term of this patent is extended or adjusted under 35 U.S.C. 154(b) by 1125 days.

(21) Appl. No.: 17/050,106

(22) PCT Filed: May 6, 2019

(86) PCT No.: PCT/IB2019/053674
§ 371 (c)(1),
(2) Date: Oct. 23, 2020

(87) PCT Pub. No.: WO2019/215572
PCT Pub. Date: Nov. 14, 2019

(65) Prior Publication Data
US 2021/0100925 A1 Apr. 8, 2021

(30) Foreign Application Priority Data

May 8, 2018 (IT) .................. 102018000005174
Apr. 23, 2019 (IT) .................. 102019000006250

(51) Int. Cl.
*A61L 15/22* (2006.01)
*A61F 13/00* (2024.01)
(Continued)

(52) U.S. Cl.
CPC ........ *A61L 15/225* (2013.01); *A61F 13/0206* (2013.01); *A61L 15/425* (2013.01);
(Continued)

(58) Field of Classification Search
CPC .................................................. A61F 13/0206
See application file for complete search history.

(56) References Cited

U.S. PATENT DOCUMENTS 5,480,717 A * 1/1996 Kundel .................. A61L 15/58
428/338
5,941,840 A * 8/1999 Court .................. A61F 13/0206
602/56

(Continued)

FOREIGN PATENT DOCUMENTS

EP 702699 A1 * 3/1996 ........... A61K 31/737

OTHER PUBLICATIONS

International Search Report, issued in PCT/IB2019/053674, dated Aug. 27, 2019.
(Continued)

*Primary Examiner* — Jessica Arble
(74) *Attorney, Agent, or Firm* — Birch, Stewart, Kolasch & Birch, LLP

(57) ABSTRACT

Adhesive wound dressing that comprises an absorbent matrix (A) adhering to the central portion of a polyurethane backing (B) having an adhesive layer for the skin, said matrix (A) comprising: a. a breathable and porous polyethylene film at the end designed to come into contact with the wound; b. an absorbent layer made of non-woven fabric adjacent to film a), said absorbent layer consisting of: i. 60-65% viscose ii. 25-30% polyester iii. 5-15% polypropylene; c. a layer of polyethylene inserted between layer b) and a layer d. of hydrophobic polystyrene, the latter being in contact with the central portion of polyurethane backing (B); wherein matrix (A) is impregnated with a solution of one or more polysaccharides or the salts thereof.

14 Claims, 1 Drawing Sheet

(51) Int. Cl.
*A61F 13/0206* (2024.01)
*A61L 15/42* (2006.01)
*A61L 15/44* (2006.01)
*A61L 15/58* (2006.01)

(52) U.S. Cl.
CPC ............... *A61L 15/44* (2013.01); *A61L 15/58* (2013.01); *A61F 2013/00157* (2013.01); *A61L 2300/104* (2013.01); *A61L 2300/106* (2013.01); *A61L 2300/252* (2013.01); *A61L 2300/254* (2013.01); *A61L 2300/30* (2013.01); *A61L 2300/402* (2013.01); *A61L 2300/406* (2013.01); *A61L 2300/41* (2013.01); *A61L 2300/42* (2013.01)

(56) References Cited

U.S. PATENT DOCUMENTS

| | | | | |
|---|---|---|---|---|
| 2009/0155362 | A1* | 6/2009 | Longin | A61K 9/0048 |
| | | | | 424/484 |
| 2011/0313383 | A1* | 12/2011 | Hofstetter | A61F 13/00 |
| | | | | 604/372 |
| 2016/0166726 | A1 | 6/2016 | Gergonne et al. | |

OTHER PUBLICATIONS

Longinotti, "The use of hyaluronic acid based dressings to treat burns: A review", Burns & Trauma, Oct. 2014, vol. 2, Issue 4, pp. 162-168.
Written Opinion of the International Searching Authority, issued in PCT/IB2019/053674, dated Aug. 27, 2019.

* cited by examiner

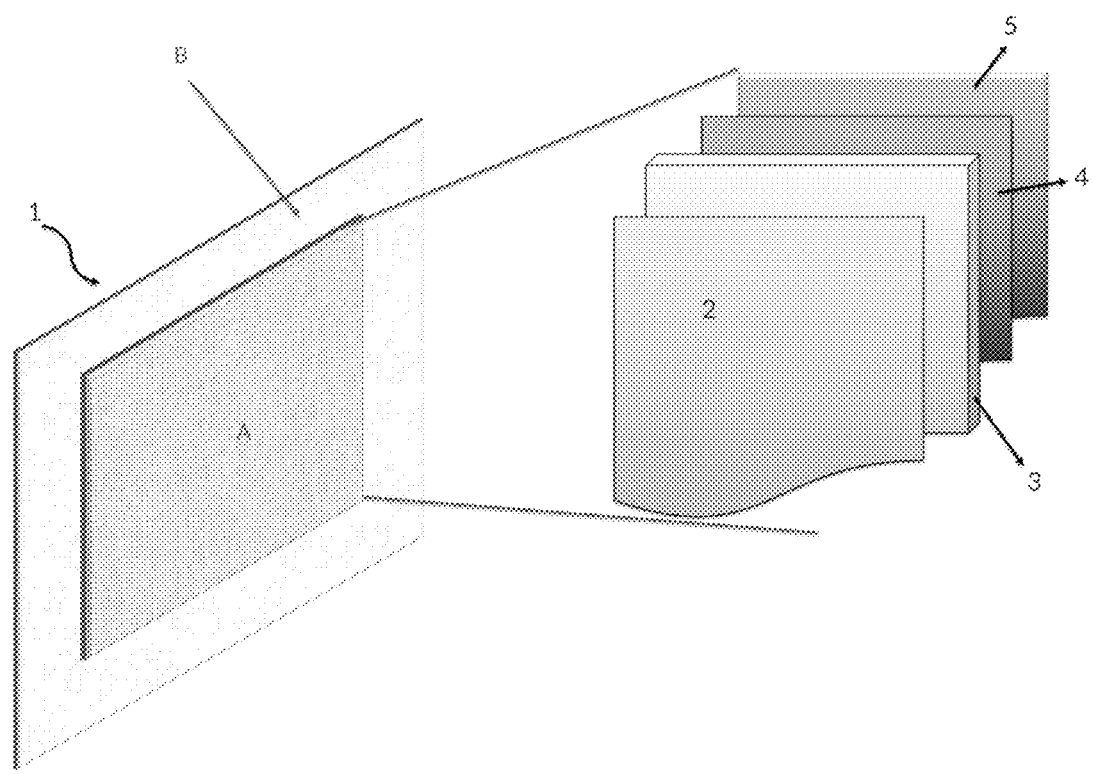

WOUND DRESSING FOR TREATMENT OF DAMAGED SKIN

BRIEF DESCRIPTION OF THE DRAWINGS

The present invention will become more fully understood from the detailed description given below and the accompanying drawings that are given by way of illustration only and are thus not limitative of the present invention.

The FIGURE illustrates an embodiment of the wound dressing of the present invention.

The invention relates to an adhesive wound dressing comprising a matrix into which a polysaccharide is absorbed.

PRIOR ART

Medical treatment of wounds should always enable the skin to heal completely, whether it is damaged by mechanical trauma, surgical wounds, ulcers or burns; effective tissue repair (i.e. without surgical complications) is possible when the wound is enabled to express its biological/biochemical potential as fully as possible with the sole aid of dressings. Wound dressings can be divided into two categories: conventional and advanced.

"Conventional wound dressing" means a material placed in direct contact with the wound which has the sole function of haemostasis, coverage and protection (viscose or cotton pads or gauze), while "advanced wound dressings" consist of biocompatible material which interacts with the site of the wound to stimulate a specific reaction directly and/or indirectly, and thus achieve rapid healing.

The "optimum" conditions that said advanced wound dressings must create to ensure rapid, correct tissue repair are:
- maintenance of a moist microenvironment at the interface between wound and dressing (said microenvironment allows migration of the fibroblast cells situated at the edges and base of the wound, enabling them to move rapidly towards the centre of the wound, thus promoting regeneration of the damaged tissue),
- thermal insulation of the damaged skin,
- absorption of excess exudate,
- pain control,
- protection against exogenous infections,
- the greatest possible comfort for the patient (as the dressing does not need to be changed so often), and finally, they must not cause trauma on removal.

The main classes of advanced wound dressings are alginates, hydrocolloids, hydrofibres and polyurethane foams.

Alginates are calcium and/or sodium-based dressings which interact with the exudate of the lesion to form a soft gel, which keeps the wound-healing environment moist.

Hydrocolloids are semiocclusive dressings comprising adhesives, pastes and powders of various kinds, available in different shapes and sizes and with different adhesive properties. They are impermeable to bacteria and other types of contamination and, because of their low permeability, can promote autolytic debridement.

Hydrofibres are sodium carboxymethyl cellulose (CMC) fibres which rapidly absorb (and therefore retain) liquids; said dressing immediately interacts with the exudate and, due to its conversion to a cohesive gel, creates a moist environment on the wound.

Polyurethane films are transparent films consisting of a semipermeable adhesive polyurethane membrane of varying sizes and thicknesses. They are impermeable to water, bacteria and contaminants in general, but allow water vapour to cross the skin barrier. Said dressings thus maintain a moist environment, promoting the formation of granulation tissue and autolysis of necrotic tissue, but do not possess any absorbent power, unlike polyurethane foams, which are also absorbent.

Some types of advanced wound dressings may also possess specific antimicrobial properties because they contain a local antiseptic; those most commonly used are iodine and silver, which are particularly suitable for wounds with a moderate or high production of exudate.

Said wound dressings very often require an additional ("secondary") dressing to secure the first dressing, which is non-adhesive.

As discussed above, the possible alternatives to surgical treatment are advanced wound dressings designed to maintain the correct degree of moisture in the wound microenvironment and, when possible, to promote the largest possible number of "optimum" conditions to ensure rapid, correct healing of the damaged skin; however, said dressings do not contain agents which are biologically active in terms of promoting the healing process correctly and without scarring, because in this case we would be defining a "biomaterial", namely a biocompatible, bioresorbable material that interfaces actively with biological systems, which may be tissues, micro-organisms or organs.

In the biomedical field, there is said to be a dual interaction between the biomaterial and the receiving organism: the biomaterial generates a biological response by the organism, which in turn causes a breakdown process in the biomaterial, and these interactions take place at different levels, i.e. at the physicochemical, molecular and cell levels. The operational environment of the biomaterial is physiological, characterised by considerable chemical activity, because said biomaterials come into direct contact with the biological fluids, namely water, enzymes, proteins and cells. Hyaluronic acid (HA) and the biocompatible derivatives thereof are among the most important biomaterials, which are mainly used in the field of wound healing and viscosupplementation of osteoarthritis.

(HA) is a heteropolysaccharide which consists of alternating residues of D-glucuronic acid and N-acetyl-D-glucosamine. It is a straight-chain polymer with a molecular weight ranging between 50,000 and $13 \times 10^6$ Da, depending on the source from which it is obtained and the preparation methods used. It is present in pericellular gels, in the ground substance of the connective tissue of vertebrates (of which it is one of the main constituents), in the synovial fluid of the joints, in vitreous humour and in the umbilical cord.

HA plays an important role in biological organisms, especially as a mechanical support for the cells of many tissues, such as skin, tendons, muscles and cartilage. It is also known that HA, through its CD44 membrane receptor, modulates many different processes relating to cell physiology and biology, such as cell proliferation, migration and differentiation, and angiogenesis.

It has therefore been demonstrated that HA plays a crucial part in the tissue repair process both from the structural standpoint (i.e. in the organisation of the extracellular matrix and regulation of its hydration) and as a substance that stimulates a wide range of biological processes wherein it is directly or indirectly involved (neovascularisation and re-epithelialisation) (Weigel P. et al., *J Theoretical Biol*, 1986: 219-234; Abatangelo G. et al., *J Surg Res*, 1983, 35:410-416; Goa K. et al., *Drugs*, 1994, 47:536-566).

In view of all these properties, which are widely recognised, HA has long been used in the preparation of biomaterials and pharmaceutical compositions, mainly in the form of creams or gels, for the treatment of wounds, ulcers and skin lesions of various origins. Moreover, said polysaccharide is also widely used in pharmaceutical and/or dermocosmetic compositions for the treatment of inflammatory skin problems such as eczema and psoriasis, or in cases of skin relaxation, due to its well-known hydrating properties.

DESCRIPTION OF THE INVENTION

The object of the present invention is an adhesive wound dressing that combines the characteristics of advanced wound dressings, as defined above, with the characteristics and benefits of a biomaterial, thus avoiding the need for a secondary dressing due to its adhesive capacity, which is not currently found in any of the biomaterials used for wound healing.

The wound dressing of the invention preferably comprises, as active agent, hyaluronic acid (HA) sodium salt or a derivative thereof having a specific average molecular weight (MW), which creates the optimum conditions for migration of the fibroblasts from the edges to the centre of the wound, thus stimulating their proliferation, accelerates the macrophagic response (the presence of macrophages is essential for correct wound healing), and performs its well-known hydrating, anti-inflammatory and painkilling activity.

The wound dressing of the invention comprises an absorbent matrix (A) adhering to the central portion of a polyurethane backing (B) having an adhesive layer for the skin, said matrix (A) comprising:
  a. a breathable, porous polyethylene film, the surface whereof is intended to come into contact with the wound, wherein said film does not adhere to the wound;
  b. an absorbent layer made of non-woven fabric adjacent to film a), said absorbent layer consisting of:
    i. 60-65% viscose
    ii. 25-30% polyester
    iii. 5-15% polypropylene;
  c. a layer of adhesive polyethylene inserted between layer b) and a layer
  d. of hydrophobic polystyrene, the latter being in contact with the central portion of polyurethane backing (B),
  wherein matrix (A) is impregnated with a solution of one or more optionally salified polysaccharides.

As shown in the FIGURE, the wound dressing 1 of the invention comprises an absorbent matrix (A) adhering to the central portion of a polyurethane backing (B) having an adhesive layer for the skin, said matrix (A) comprising:
  a. a breathable, porous polyethylene film 2, the surface whereof is intended to come into contact with the wound, wherein said film does not adhere to the wound;
  b. an absorbent layer 3 made of non-woven fabric adjacent to film a), said absorbent layer consisting of:
    i. 60-65% viscose
    ii. 25-30% polyester
    iii. 5-15% polypropylene;
  c. a layer of polyethylene 4 inserted between layer b) and a layer
  d. of hydrophobic polystyrene 5, the latter being in contact with the central portion of polyurethane backing (B),
  wherein matrix (A) is impregnated with a solution of one or more optionally salified polysaccharides.

Due to its particular structure and materials, the wound dressing of the invention is permeable to water vapour and easy to remove without skin trauma, and has a strong, transparent, waterproof backing (B).

The wound dressing of the invention has the following properties:
  it ensures the maintenance of a moist microenvironment at the wound-dressing interface (for as long as it remains in contact with the wound), stimulating fibroblast proliferation and therefore correct, rapid wound healing,
  it prevents adherence between new granulation tissue and the matrix placed in direct contact with the wound (if the adherence is not kept moist, it may give rise to a "dry" eschar that traps the new granulation tissue),
  it only adheres to the undamaged part surrounding the damaged tissue, and is easy to remove without trauma,
  it promotes and guarantees:
  thermal insulation of the damaged skin, ensuring correct breathability,
  absorption of excess exudate,
  pain control,
  protection against exogenous infections,
  greater comfort for the patient, as fewer dressing changes are required than with the currently known dressings.

Due to its specific conformation and the presence of the polysaccharide, the wound dressing of the invention actively promotes correct skin regeneration, facilitates a rapid wound-healing process, protects the wound against microbial contamination, controls pain and prevents the formation of hypertrophic scars. The wound dressing therefore has all the characteristics of a biomaterial, and does not require a secondary dressing.

The polysaccharides that can be used for the purposes of the invention comprise glycosaminoglycans, chitin, chitosan, pectin, pectinic acid, galactans, alginic acid and alginates, glucans, natural gums, fructans, polymannans, carrageenan and derivatives of said polysaccharides.

Examples of glycosaminoglycans include hyaluronic acid and/or derivatives thereof such as salts, esters, amides and sulfated hyaluronic acid; hybrid complexes of high- and low-molecular-weight hyaluronic acid (described in WO2012/032151); chondroitin, chondroitin sulfate, dermatan sulfate, keratan sulfate, heparan sulfate, heparin and heparinoids.

An example of a chitosan derivative is chitosan derivatised with lactose (described in WO2007/135116 and WO2017/211776).

Examples of galactans include agar and agarose. Examples of glucans include dextran, dextrin, trehalose, maltose, starch, cellulose and derivatives thereof, preferably hydroxyethylcellulose, carboxymethylcellulose, hydroxymethylcellulose and cellulose acetate.

Examples of natural gums include gellan gum and xanthan gum. A preferred fructan is inulin.

A preferred polysaccharide is hyaluronic acid sodium salt or derivatives thereof prepared from hyaluronic acid obtained from any source, for example by extraction from rooster combs (EP138572), by fermentation (from *Streptococcus equi* or *zooepidemicus*, EP716688), or by biosynthesis (from *Bacillus*, EP2614088). The average molecular weight ranges between 400 and $3\times10^6$ Da, in particular between $1\times10^5$ Da and $1\times10^6$ Da, even more particularly between 150,000 and 250,000 Da and/or between 500,000 and $1\times10^6$ Da.

The most preferred polysaccharides are hyaluronic acid sodium salt with an average molecular weight ranging between 150 and 250 kDa, hybrid complexes of low- and high-molecular-weight hyaluronic acids wherein the high-molecular-weight hyaluronic acid ranges between 1100 and 1400 kDa and the low-molecular-weight hyaluronic acid ranges between 80 and 100 kDa, and chitosan derivatized with lactose.

"Average molecular weight" (MW) here means the weight-average MW, calculated by the "intrinsic viscosity" method (Terbojevich et al., *Carbohydr Res*, 1986, 363-377).

The HA derivatives that can be used to form the matrix of the wound dressing of the invention comprise:

HYAFF®: HA esters with alcohols of the aliphatic, arylaliphatic, cycloaliphatic, aromatic, cyclic and heterocyclic series, preferably benzyl ester with an esterification percentage preferably ranging between 1 and 50%, while the remaining percentage of non-esterified HA can be salified with sodium (EP216453);

HYADD®: HA amides with amines of the aliphatic, arylaliphatic, cycloaliphatic, aromatic, cyclic and heterocyclic series, preferably HA hexadecyl amide with an amidation percentage ranging between 0.1 and 5%, while the remaining percentage of non-amidated HA can be salified with sodium (EP1095064);

O-sulfated derivatives of HA up to the 4th degree of sulfation, preferably grade 1 or grade 3 (EP702699, WO2017085622);

ACP®: inner esters of HA with an esterification percentage ranging between 0.05 and 5%, while the remaining percentage of non-esterified HA can be salified with sodium (EP341745);

HYOXX™: percarboxylated derivatives of HA obtained by oxidation of the primary hydroxyl of the N-acetylglucosamine fraction with a degree of percarboxylation ranging between 0.1 and 100%, preferably between 2 and 5%. All the carboxyl groups of HA can be salified with sodium (EP1339753).

The adhesive layer of polyurethane backing (B) (last outer layer) is preferably a layer of polyacrylic glue; said layer ensures both adherence to the matrix and adherence to the skin in the areas surrounding matrix (A).

Matrix (A), characterised by a high absorption capacity, is moist because it is impregnated with an aqueous solution comprising a polysaccharide as active agent, preferably hyaluronic acid sodium salt (NaHA) or a derivative thereof, combined with suitable excipients; the concentration of the polysaccharide or the HA salt or HA derivative ranges between 0.1% and 1% w/w, preferably between 0.2% and 0.6% w/w. The solution can also include other ingredients such as solvents, preservatives and pH correctors. Examples of said ingredients include glycerol, propylene glycol, 2-phenylethanol, ethylhexylglycerin, lactic acid and other excipients suitable for topical application.

The preferred active agent is hyaluronic acid sodium salt, NaHA, prepared from an HA produced by fermentation from *Streptococcus*, at a concentration ranging between 0.1% and 1% w/w and preferably between 0.2% and 0.6% w/w, with an average MW preferably ranging between 150,000 and 250,000 Da and/or between 500,000 and $1 \times 10^6$ Da, or a derivative thereof, preferably grade 3 O-sulfated hyaluronic acid, HAS; NaHA with an average MW ranging between 150,000 and 250,000 Da at the concentration of 0.3% w/w is most preferred as active agent.

An example of a solution which can be used according to the invention for absorption on matrix (A) has the composition shown in Table A:

TABLE A

| | Quantity: g/100 g |
|---|---|
| Active agent: | |
| NaHA or its derivative | 0.1-1.0 |
| Excipients | |
| Glycerol | 20-30 |
| 1,3-propanediol (propylene glycol) | 2-6 |
| Lactic acid | 0.0002-0.0006 q.s. to pH 5.5 |
| 2-phenylethanol | 0.4-0.8 |
| Ethylhexylglycerin | 0.04-0.08 |
| Purified water | q.s. to 100 g |

The solutions can optionally contain additional pharmacologically/biologically active plant-based or synthetic substances. Examples of pharmacologically/biologically active substances include medicaments for topical use such as NSAIDs and steroids; antibacterials/antibiotics, preferably iodine, silver sulfadiazine or metallic silver; cytostatics; growth factors; fibrinolytics and antioedema agents; proteolytic enzymes, preferably collagenase, hyaluronidase; anticoagulants; proteins such as collagen or silk proteins such as fibroin; local anaesthetics such as lidocaine; *Triticum vulgare* extract; and absorbent polymers such as CMC. The matrix of the wound dressing of the invention is impregnated to 50% of its maximum absorption capacity by homogeneous spraying of the aqueous solution containing the active agent, such as the solution described in Table A; said matrix is then impregnated with 65±5 mg/cm$^2$. A matrix with a size of 25 cm$^2$ therefore contains 1.67 g of said liquid composition.

The matrix typically has an average thickness of 2.5 (±0.3) to 3.0 (±0.3) mm, preferably 2.7±0.3 mm, with an absorbent power (of liquids)≥20 g/100 cm$^2$ in a time of ≤1 sec.

The preferred composition of the absorbent layer of non-woven fabric is 60% viscose, 25% polyester and 15% polypropylene (percentages by weight).

A particularly preferred solution which can be used according to the invention to be absorbed on the absorbent layer of 60% viscose, 25% polyester and 15% polypropylene has the composition shown in Table B:

TABLE B

| | Quantity: g/100 g |
|---|---|
| Active agent: | |
| NaHA with an average MW ranging between 150,000 and 250,000 Da | 0.3 |
| Excipients | |
| Glycerol | 25 |
| 1,3-propanediol (propylene glycol) | 4 |
| Lactic acid | 0.0005 q.s. to pH 5.5 |
| 2-phenylethanol | 0.54 |
| Ethylhexylglycerin | 0.06 |
| Purified water | q.s. 100 g |

Matrix (A) which, in its preferred form, adheres to the adhesive polyurethane backing with polyacrylic glue, possesses an average thickness of 2.7±0.3 mm and an absorbent power≥20 g/100 cm$^2$ in a time of ≤1 sec, and is impregnated to 50% of its maximum absorption capacity by homogeneous spraying of 65±5 mg/cm$^2$ of the liquid pharmaceutical composition described in Table B.

The wound dressings of the invention are useful for surgical use in the treatment of wounds, burns, ulcers of different origin, slight or moderate abrasions, and all skin lesions requiring the use of an advanced dressing.

The wound dressings of the invention are also useful for dermatological use in the treatment of local inflammations which can cause skin lesions or microlesions such as psoriasis, various forms of inflammatory dermatitis, atopic dermatitis and irritative contact dermatitis, and eczema of various exogenous or endogenous origins.

The wound dressings of the invention are also useful for dermocosmetic use in the treatment of skin relaxation with or without lesions or microlesions, due to the high hydrating power of the polysaccharide, in particular of the HA sodium salt, and the ability to stimulate all the physiological functions of the fibroblasts which lead (over time) not only to skin hydration, but also to regeneration of the skin tissue, which compacts due to increased collagen production by the treated skin fibroblasts.

The invention claimed is:

1. Adhesive wound dressing which comprises an absorbent matrix (A) adhering to a central portion of a polyurethane backing (B) having an adhesive layer for the skin, said matrix (A) comprising:
   a. a breathable and porous polyethylene film at the surface thereof designed to come into contact with the wound;
   b. an absorbent non-woven fabric layer adjacent to film a), said absorbent layer consisting of:
      i. 60-65% viscose
      ii. 25-30% polyester
      iii. 5-15% polypropylene;
   c. a polyethylene layer inserted between layer b) and a layer
   d. of hydrophobic polystyrene, the latter being in contact with the central portion of polyurethane backing (B);
   wherein matrix (A) is impregnated with a solution of hyaluronic acid sodium salt with an average molecular weight ranging from 150,000 to 250,000 Da in a concentration from 0.1% to 1% w/w.

2. Wound dressing according to claim 1 wherein the adhesive layer of backing (B) is a layer of polyacrylic glue.

3. Wound dressing according to claim 1 wherein absorbent layer b) consists of:
   i. 60% viscose;
   ii. 25% polyester;
   iii. 15% polypropylene.

4. Wound dressing according to claim 1 wherein the hyaluronic acid sodium salt is present in a concentration of 0.3% w/w.

5. Wound dressing according to claim 1 wherein matrix (A) has an average thickness ranging from 2.5 (±0.3) to 3.0 (±0.3) mm.

6. Wound dressing according to claim 5 wherein matrix (A) is impregnated to 50% of its maximum absorption capacity by homogeneous spraying of 65±5 mg/cm$^2$ of the solution containing hyaluronic acid sodium salt.

7. Wound dressing according to claim 6 wherein matrix (A) has an average thickness of 2.7±0.3 mm and an absorption power ≥20 g/100 cm$^2$ in a time ≤1 sec.

8. Wound dressing according to claim 1 wherein absorbent layer b) consists of 60% viscose, 25% polyester and 15% polypropylene, matrix (A) has an average thickness of 2.7±0.3 mm and an absorbent power ≥20 g/100 cm$^2$ in a time of ≤1 sec, and is impregnated to 50% of its maximum absorption capacity by homogeneous spraying of 65±5 mg/cm$^2$ of a solution of hyaluronic acid sodium salt with an average molecular weight ranging between 150,000 and 250,000 Da at the concentration of 0.3% w/w.

9. Wound dressing according to claim 1 wherein matrix (A) contains pharmacologically/biologically active substances selected from iodine, silver sulfadiazine, metallic, colloidal or micronised silver, antibiotics for topical use, local anaesthetics, NSAIDs, steroids for topical use, cytostatics, growth factors, fibrinolytics and antioedema agents, proteolytic enzymes, collagenase, hyaluronidase, anticoagulants, proteins or silk proteins, and *Triticum vulgare* extract.

10. Wound dressing according to claim 1 for surgical use in the treatment of wounds, burns, ulcers of various kinds, abrasions, and slight or moderate grazes.

11. Wound dressing according to claim 1 for dermatological use in the treatment of local inflammations that may cause skin lesions or microlesions.

12. Wound dressing according to claim 1 for dermocosmetic use in the treatment of skin relaxation with or without lesions or microlesions.

13. Wound dressing according to claim 2 wherein absorbent layer b) consists of:
   i. 60% viscose;
   ii. 25% polyester;
   iii. 15% polypropylene.

14. Wound dressing according to claim 1 wherein matrix (A) contains pharmacologically/biologically active substances selected from collagen and fibroin.

* * * * *